(12) United States Patent
Wensley et al.

(10) Patent No.: US 10,898,660 B2
(45) Date of Patent: Jan. 26, 2021

(54) METHODS AND DEVICES FOR MODULATING AIR FLOW IN DELIVERY DEVICES

(71) Applicant: FONTEM HOLDINGS 1 B.V., Amsterdam (NL)

(72) Inventors: Martin Wensley, Los Gatos, CA (US); Michael Hufford, Chapel Hill, NC (US); Peter Lloyd, Walnut Creek, CA (US)

(73) Assignee: FONTEM HOLDINGS 1 B.V., Amsterdam (NL)

( * ) Notice: Subject to any disclaimer, the term of this patent is extended or adjusted under 35 U.S.C. 154(b) by 672 days.

(21) Appl. No.: 15/509,853

(22) PCT Filed: Sep. 10, 2015

(86) PCT No.: PCT/US2015/049349
§ 371 (c)(1),
(2) Date: Mar. 8, 2017

(87) PCT Pub. No.: WO2016/040575
PCT Pub. Date: Mar. 17, 2016

(65) Prior Publication Data
US 2017/0246405 A1 Aug. 31, 2017

Related U.S. Application Data

(60) Provisional application No. 62/048,791, filed on Sep. 10, 2014.

(51) Int. Cl.
*A61M 11/00* (2006.01)
*A24F 47/00* (2020.01)
(Continued)

(52) U.S. Cl.
CPC ......... *A61M 11/001* (2014.02); *A24F 47/008* (2013.01); *A61M 11/002* (2014.02);
(Continued)

(58) Field of Classification Search
CPC ............. A61M 11/001; A61M 11/002; A61M 11/042; A61M 15/002; A61M 15/0086;
(Continued)

(56) References Cited

U.S. PATENT DOCUMENTS 2,057,353 A 10/1936 Whittemore
4,446,862 A 5/1984 Baum et al.
(Continued)

FOREIGN PATENT DOCUMENTS

CN 1541577 A 11/2004
CN 202014571 U 10/2011
(Continued)

OTHER PUBLICATIONS

Extended European Search Report for European Patent Application No. 15740106.8; dated Sep. 26, 2017; 9 pages.
(Continued)

*Primary Examiner* — Samchuan C Yao
*Assistant Examiner* — Nathan M Le
(74) *Attorney, Agent, or Firm* — Perkins Coie LLP; Kenneth H. Ohriner (57) ABSTRACT

A device for generating a condensation aerosol includes (a) vaporization chamber having an upstream first inlet and a downstream outlet; (b) a heater element in the vaporization chamber between the upstream first inlet and the downstream outlet; (c) an airflow path in fluid communication with the vaporization chamber, wherein the airflow path comprises a second inlet configured to permit a substantially laminar flow of air into the airflow path, wherein the second inlet is downstream of the heater element; and (d) the device
(Continued)

Baffle slider used to divert air around heater and vaporization region having components or apparatus on or in the device for changing air flow in the vaporization chamber. Changing the air flow in the vaporization chamber may be used to change the particle size of a condensation aerosol produced in the vaporization chamber, and/or to change the amount of visible vapor emitted from the device.

2 Claims, 8 Drawing Sheets

(51) Int. Cl.
*A61M 11/04* (2006.01)
*A61M 15/00* (2006.01)
*A61M 15/06* (2006.01)
*A61M 16/10* (2006.01)

(52) U.S. Cl.
CPC ........ *A61M 11/042* (2014.02); *A61M 15/002* (2014.02); *A61M 15/0086* (2013.01); *A61M 15/06* (2013.01); *A61M 16/1085* (2014.02); *A61M 2205/3334* (2013.01); *A61M 2205/3592* (2013.01); *A61M 2205/50* (2013.01); *A61M 2205/502* (2013.01); *A61M 2206/11* (2013.01); *A61M 2230/40* (2013.01)

(58) Field of Classification Search
CPC .............. A61M 15/06; A61M 16/1085; A61M 2205/3334; A61M 2205/3592; A61M 2205/50; A61M 2205/502; A61M 2206/11; A61M 2230/40; A61M 15/0031; A61M 16/1075; A61M 16/108; A24F 47/008; A24F 40/00; A24F 40/10; A24F 40/20; A24F 40/46; A24F 40/50; A24F 40/57; A24D 3/041; B01F 3/04078; B01F 15/06; B01F 3/04014; B01F 2015/062
See application file for complete search history.

(56) References Cited

U.S. PATENT DOCUMENTS 4,735,217 A * 4/1988 Gerth .................... A24F 47/008 128/203.17
4,953,572 A 9/1990 Rose et al.
5,487,378 A 1/1996 Robertson et al.
5,666,977 A 9/1997 Higgins et al.
5,743,251 A 4/1998 Howell et al.
5,894,841 A 4/1999 Voges
6,116,237 A 9/2000 Schultz et al.
6,155,268 A 12/2000 Takeuchi
6,196,218 B1 * 3/2001 Voges .................. A24F 47/002 128/200.14
6,234,167 B1 5/2001 Cox et al.
6,443,146 B1 9/2002 Voges
6,516,796 B1 2/2003 Cox et al.
6,598,602 B1 7/2003 Sjoholm
6,804,458 B2 10/2004 Sherwood et al.
6,923,179 B2 8/2005 Gupta et al.
7,128,067 B2 10/2006 Byron et al.
7,167,776 B2 1/2007 Maharaji et al.
7,743,766 B2 6/2010 Gupta et al.
7,913,688 B2 3/2011 Cross et al.
8,156,944 B2 4/2012 Plan
8,794,231 B2 8/2014 Thorens et al.
8,910,640 B2 12/2014 Sears et al.
8,948,578 B2 2/2015 Buchberger
9,072,321 B2 7/2015 Liu
9,414,629 B2 8/2016 Egoyants et al.
9,420,829 B2 8/2016 Thorens et al.
9,427,711 B2 8/2016 Terry et al.
9,510,623 B2 12/2016 Tucker et al.
9,609,893 B2 4/2017 Novak, III et al.
9,609,894 B2 4/2017 Abramov et al.
9,668,523 B2 6/2017 Tucker et al.
9,687,027 B2 6/2017 Poston et al.
9,713,346 B2 7/2017 Hon
2003/0108342 A1 6/2003 Sherwood et al.
2003/0168057 A1* 9/2003 Snyder ................ A61M 15/002 128/200.21
2004/0025865 A1 2/2004 Nichols et al.
2004/0079368 A1 4/2004 Gupta et al.
2004/0099266 A1* 5/2004 Cross .................. A61M 11/002 128/203.12
2004/0129793 A1 7/2004 Nguyen et al.
2005/0004520 A1* 1/2005 Lemoine ............ A61M 1/0047 604/118
2005/0016550 A1* 1/2005 Katase .................. A24F 47/002 131/194
2005/0235991 A1 10/2005 Nichols et al.
2005/0268911 A1* 12/2005 Cross .................. A61M 11/002 128/204.17
2006/0047368 A1 3/2006 Maharajh et al.
2006/0249144 A1 11/2006 DeHaan et al.
2007/0044793 A1* 3/2007 Kleinstreuer ..... A61M 15/0086 128/200.21
2008/0110454 A1* 5/2008 White ................. A61M 11/041 128/200.23
2008/0245368 A1* 10/2008 Dunsmore .......... A61M 16/127 128/205.24
2008/0264416 A1 10/2008 Gonda et al.
2009/0188490 A1 7/2009 Han
2009/0196930 A1 8/2009 Surber et al.
2010/0181387 A1* 7/2010 Zaffaroni ............ A61M 11/001 239/13
2011/0094523 A1* 4/2011 Thorens ................ A61M 15/06 131/194
2011/0120456 A1 5/2011 Immel
2011/0123626 A1* 5/2011 Weers .................. A61K 9/0075 424/489
2011/0233043 A1 9/2011 Cross et al.
2011/0277757 A1 11/2011 Terry et al.
2012/0006342 A1 1/2012 Rose et al.
2012/0186594 A1* 7/2012 Liu ....................... A24F 47/008 131/329
2013/0032139 A1 2/2013 Hale et al.
2013/0180525 A1 7/2013 Cross et al.
2013/0213418 A1* 8/2013 Tucker .................. A24F 47/008 131/328
2013/0284192 A1* 10/2013 Peleg .................... A24F 47/002 131/329
2013/0340775 A1* 12/2013 Juster ...................... H04L 67/42 131/273
2014/0144429 A1 5/2014 Wensley et al.
2014/0190496 A1 7/2014 Wensley et al.
2014/0202472 A1* 7/2014 Levitz ..................... A24F 13/22 131/187
2014/0207016 A1 7/2014 Addington et al.
2014/0283855 A1 9/2014 Hawes et al.
2014/0350028 A1 11/2014 Weers et al.
2015/0196060 A1 7/2015 Wensley et al.
2016/0213065 A1* 7/2016 Wensley .................. H05B 3/46
2016/0324212 A1 11/2016 Cameron

FOREIGN PATENT DOCUMENTS

CN 102655773 A 9/2012
DE 202010002041 U1 5/2010
EP 1618803 A1 1/2006
EP 2047880 A1 4/2009
EP 2113178 A1 11/2009
WO 2005025654 A1 3/2005
WO 2012026963 A2 3/2012
WO 2013083635 A1 6/2013

(56) References Cited

FOREIGN PATENT DOCUMENTS

WO          2013083636 A1    6/2013
WO    WO-2013083636 A1 *  6/2013   ........... A24F 47/008

OTHER PUBLICATIONS

State Intellectual Property Office, Office Action for Chinese Application No. 201580014558.8; dated Jun. 5, 2019; 23 pages.
United States Patent and Trademark Office, International Search Report and Written Opinion for PCT/US2015/049349, dated Dec. 18, 2015, 13 pages.

* cited by examiner

METHODS AND DEVICES FOR MODULATING AIR FLOW IN DELIVERY DEVICES

BACKGROUND

There is a need for new methods and devices for administering compounds, such as pharmaceutical agents, to a subject. In particular, there is a need for methods and devices for delivery of compounds to a subject where the compounds are aerosolized to fall within a specified particle size range. In some cases, particles within a specified size range can be efficiently delivered to the deep lung. For example, there is an urgent need for improved methods and devices to deliver nicotine to a subject in specified doses and in a specified particle range size without the carcinogens and other chemicals associated with combustible tobacco products.

BRIEF STATEMENT OF THE INVENTION

A device for generating a condensation aerosol includes (a) vaporization chamber having an upstream first inlet and a downstream outlet; (b) a heater element in the vaporization chamber between the upstream first inlet and the downstream outlet; (c) an airflow path in fluid communication with the vaporization chamber, wherein the airflow path comprises a second inlet configured to permit a substantially laminar flow of air into the airflow path, wherein the second inlet is downstream of the heater element; and (d) the device having components or apparatus on or in the device for changing air flow in the vaporization chamber. Changing the air flow in the vaporization chamber may be used to change the particle size of a condensation aerosol produced in the vaporization chamber, and/or to change the amount of visible vapor emitted from the device.

The device may include apparatus or components configured to control a size of the upstream first inlet. A mass median aerodynamic diameter (MMAD) of the condensation aerosol particles produced in the vaporization chamber may be from about 1 µm to about 3 µm, or from about 0.2 µm to about 0.6 µm. A slide may be configured to slidably cover the upstream first inlet. A removable orifice can be configured to modify the upstream first inlet. The removable orifice is optionally configured to insert into the upstream first inlet. An opening of the removable orifice may have a cross-sectional area that is less than a cross-sectional area of the upstream first inlet.

The apparatus may be electronically-controlled. A user interface may be provided in electronic communication with the apparatus, with the user interface configured to allow a user to select a condensation aerosol particle size to be produced by the device. The electronically-controlled apparatus may be configured to modify a size of the upstream first inlet. The size of the upstream first inlet may be modified by opening or closing the upstream first inlet. The device generally has a mouthpiece in fluid communication with the vaporization chamber, and a plurality of inlets upstream of the heater element. The condensation aerosol may include nicotine.

In some instances, the device has: a liquid reservoir in fluid communication with the heater element; the liquid including nicotine; the apparatus is configured to modify a size of the outlet and/or the second inlet. A baffle may be located upstream of the heater element, with the baffle configured to slide within the vaporization chamber. In some instances, the apparatus is configured to move based on a user input.

A method for modulating condensation aerosol particle size produced from a condensation aerosol generating device includes (a) providing a condensation aerosol generating device comprising (i) a vaporization chamber, wherein the vaporization chamber has an upstream first inlet and a downstream outlet; (ii) a heater element in the vaporization chamber, wherein the heater element is located between the upstream first inlet and the downstream outlet; and (iii) an airflow path in fluid communication with the vaporization chamber, wherein the airflow path comprises a second inlet configured to permit a substantially laminar flow of air into the airflow path, wherein the second inlet is downstream of the heater element; and (b) adjusting an apparatus for modulating air flow in the vaporization chamber, wherein modulation of air flow in the vaporization chamber modifies a particle size of a condensation aerosol produced in the vaporization chamber.

The size of the upstream first inlet can be modified by opening or closing the upstream first inlet.

The apparatus for modulating the upstream first inlet size and the apparatus for modulating the second inlet size can be the same, or they can be different. The apparatus for modulating a size of the upstream first inlet is a cover, for example a slidable cover configured to cover the upstream first inlet and the second inlet. The apparatus for modulating the second inlet size may control resistance through the device. Modulating the upstream first inlet size may control condensation aerosol particle size, for example to cause the device to produce condensation aerosol particles with an MMAD of from about 1 µm to about 5 µm, or with or without visible vapor. A plurality of upstream first inlets may be used.

A device for generating a condensation aerosol may include (a) a vaporization chamber configured to generate a condensation aerosol, wherein the vaporization chamber has an upstream inlet and a downstream outlet; (b) a heater element in the vaporization chamber, wherein the heater element is located between the upstream inlet and the downstream outlet; (c) a flow sensor; and (d) an apparatus to receive an inhalation profile of a user of the device, wherein the device is configured to modify a characteristic of the device based on the inhalation profile. The device may further include a user interface configured to permit a user to modify a characteristic of the device, which may provide more efficient delivery of the condensation aerosol to a deep lung of a user; cause a user of the device to exhale a lower fraction of the condensation aerosol; adjust a sensory effect, such as mouth feel or appearance, of the condensation aerosol.

Alternatively, the modified characteristic is an amount of liquid vaporized by the heater element; an amount of current applied to the heater element; or a size of the inlet. The flow sensor may be a hot wire or vane type flow meter or a pressure traducer configured to measure an inhalation vacuum. The pressure traducer, if used, may be configured to calculate an inhalation rate. The apparatus may include a microprocessor and a wireless communication device. The device can be configured to calculate optimum parameters for condensation aerosol generation based on an inhalation profile of a user. In this case, the modified characteristics can include the condensation aerosol particle size; the timing of aerosol generation in a user inhalation volume; a resistance to air flow through the device, or an inhalation rate of a user of the device.

The inhalation profile may include inhalation rates of a user over a period of time; a total volume of air inhaled; or a peak inhalation rate of a user of the device. The device may be programmed to automatically modify a characteristic of the device based on the inhalation profile, or to allow manual modification of a characteristic of the device by a user based on the inhalation profile.

DETAILED DESCRIPTION

There are multiple factors that contribute to cigarette addiction. Some of the factors include addiction to nicotine, psychological factors ranging from the smell, taste, to social associations associated with smoking. One factor driving cigarette addiction is the sensory cues associated with the inhalation and exhalation of smoke itself. Some electronic cigarettes (e-cigs) create a large amount of vapor to mimic cigarette smoke. In some cases, to avoid vapor deposition in the lung and to preclude exhalation of the vapor previous devices have been configured to provide aerosol particles that range in size between 0.2 microns and 0.6 microns. Aerosol particles between 0.2 microns and 0.6 microns are generally too small to gravitationally settle in the lung during regular breathing. Most aerosol particles between 0.2 microns and 0.6 microns can be inhaled, but are subsequently exhaled.

Provided herein are devices, systems, kits, compositions that produce an aerosol in the 1 micron to 3 micron range. Aerosol particles in the 1 micron to 3 micron range settle in the lung much more efficiently than smaller particles and are not readily exhaled. The devices and methods described herein provide an electronic cigarette that more closely replicates the nicotine deposition associated with combustible cigarettes. Devices and methods described herein provide a nicotine pharmacokinetics profile (PK) that can provide the sensory effects associated with combustible cigarette smoking.

Furthermore, respiratory drug delivery devices of the disclosure can have an internal resistance that is low enough to enable the user to inhale directly into the lung. This is generally regarded as advantageous for deep lung delivery of an agent, such as a nicotine, and to enable rapid nicotine pharmacokinetics (PK). Other combustible cigarettes can have a high enough resistance to preclude direct to lung inhalation thereby requiring the user to inhale, or puff, by using a mouth breathing maneuver.

The present device and systems can be part of an electronic agent (e.g., nicotine) delivery platform. The electronic platform for delivering an agent (e.g., nicotine) can be used to deliver the agent (e.g., nicotine) to a subject in a particular dose, with a particular mean particle size, pH, and airflow characteristics, which can affect back of the throat impaction and upper airway deposition. In one embodiment, the electronic delivery platform regulates a schedule of delivery of an agent (e.g., nicotine) to a user over time. Furthermore, provided herein are methods of tracking usage of an agent (e.g., nicotine) to suggest a dosing strategy based on the goal or goals of the user, especially relative to humans smoking tobacco or using a nicotine containing product.

Furthermore, respiratory drug delivery devices of the disclosure can have an internal resistance that is low enough to enable the user to inhale directly into the lung. This is generally regarded as advantageous for deep lung delivery of an agent, such as a nicotine, and to enable rapid nicotine pharmacokinetics (PK). Other combustible cigarettes can have a high enough resistance to preclude direct to lung inhalation thereby requiring the user to inhale, or puff, by using a mouth breathing maneuver.

In some cases, the particle size provided by a device 100 is controlled by controlling the amount of air that entrains the vaporizing nicotine mixture. Control of flow rate through the vaporization chamber 102 can be accomplished by controlling the size of the opening (orifice) 104 to the vaporization chamber. By controlling the size of the opening, the resulting particle size can be controlled. The users may vary this opening size so that they can control the particle size, and thereby affect the vaping experience in terms of the amount of visible vapor produced by the device, as well as other sensory characteristics. In some cases, a user could choose a larger particle size (1-3 um) to more closely replicate the nicotine deposition of cigarettes, as well as vape in a more discrete manner, and in another case they could choose a 0.5 um aerosol to more closely mimic the visual aspects of exhaling a visible vapor, like smoking. This can be accomplished by a user manipulated a slide 106 or other method of varying the entrance opening size as shown in FIG. 1. The product can also come with exchangeable orifices 120 that the user inserts into the device as shown in FIG. 2. Alternatively the device can have a user interface where the user selects the aerosol size and onboard electronics open or close the opening. A baffle slider 130 may be positioned upstream of a heater element 108. The baffle slider can be used to divert air around a heater element or vaporization region as shown in FIG. 3.

Smokers exhibit a wide range of inhalation profiles. There are changes between one smoker to another in inhalation rates and the total volume inhaled. Inhalation rates can also vary in different ways from the peak inhalation rate that the smoker achieves to the actual profile (e.g. an inhalation rate that starts slow compared to one that starts rapidly, as shown in FIG. 4). The efficiency of deep lung deposition is dependent on many factors such as aerosol particle size, the timing of the delivery of the aerosol to the lung (where in the inhalation volume—early vs. late) and inhalation rates. Inhalation profiles can also play a role in if and where aerosols are deposited in the respiratory tract. A more rapid inhalation rate can cause larger aerosol particles to deposit in the back of the throat, mouth and upper airway due to inertial impaction. Shallow breathers, with lower total inhalation volumes can benefit from aerosol delivered earlier in the inhalation volume allowing the aerosol to be chased into the deep lung without leaving aerosol in the mouth, throat and upper airway.

The present devices and methods allow the user to vary the resistance on a device thereby allowing a user to have a device that can either be conducive to deep lung delivery or replicate the puffing maneuver of combustible cigarettes. By varying both the size of the inlet 104 that controls the flow through the vaporization chamber 102 and the size of the bypass or secondary inlet 110, the user can control the resistance through the device 100 and the same time control the resultant aerosol particle size.

A variation of the resistance can be done over any period of time, for example a variation of the resistance can be done over a month, days, hours, or minutes. A variation of the resistance can be done within the same "smoking session." For example, a subject can select a high resistance and small particle size to more closely replicate the sensation, perception or the nicotine pharmacokinetics (PK) associated with a combustible cigarette experience. A user can select or alter a resistance/particle size after several initial deep inhalations, for example to maximize the nicotine experience within a series of inhalations (e.g., thereby reducing nicotine cravings).

Figure 1:
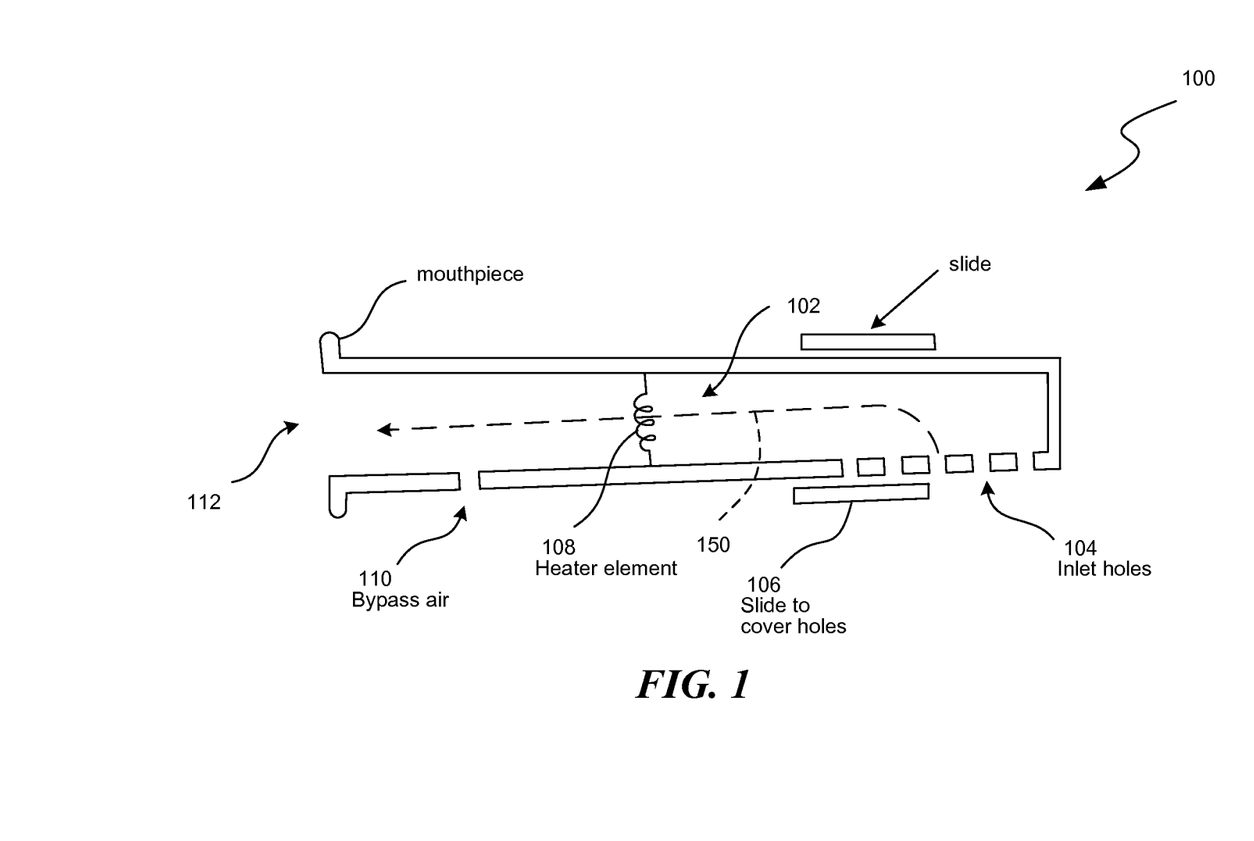
FIG. 1 illustrates a mouth piece, a bypass air, a heater element, a slide, inlet holes, and a slide of a device for generating a condensation aerosol.
Figure 2:
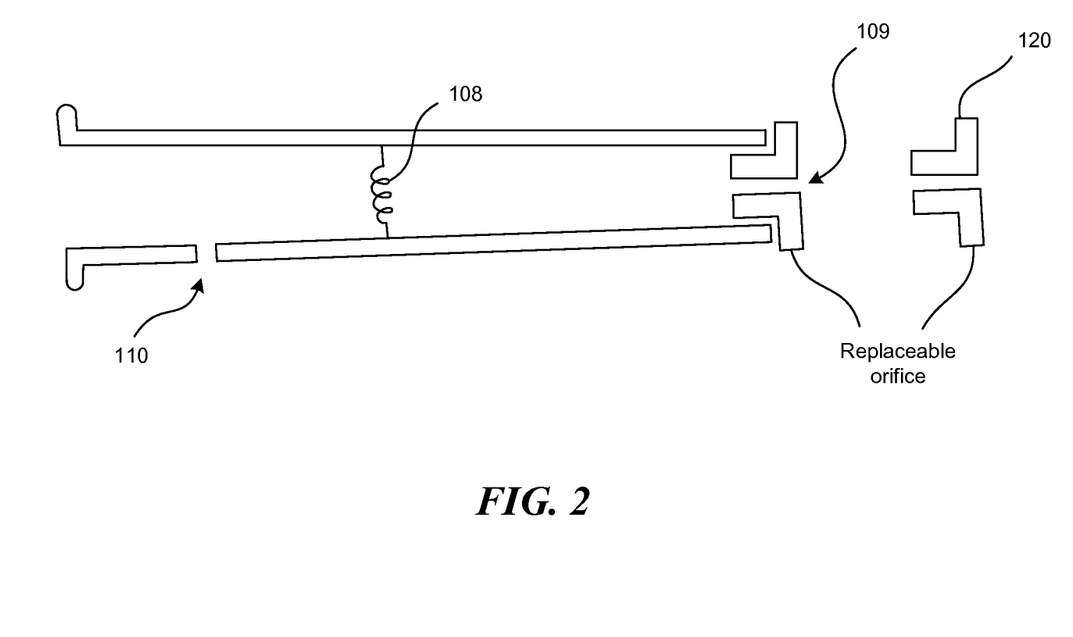
FIG. 2 illustrates a replaceable orifice of a device for generating a condensation aerosol.
Figure 3:
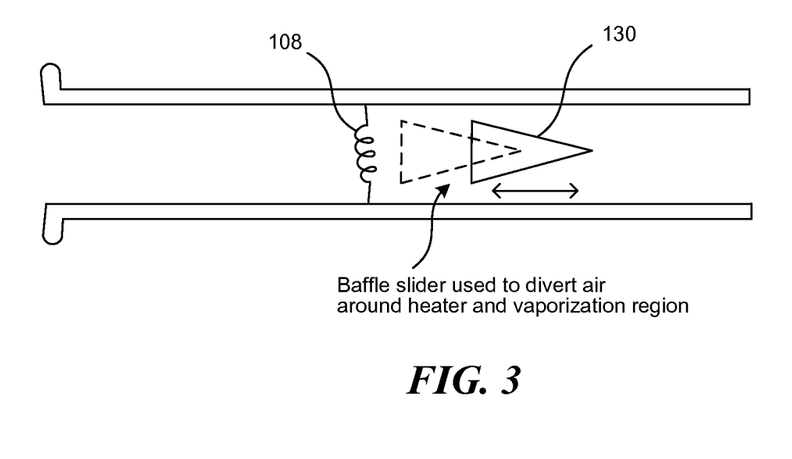
FIG. 3 illustrates a baffle slider used to modulate air flow and vaporization in a device for generating a condensation aerosol.
Figure 4:
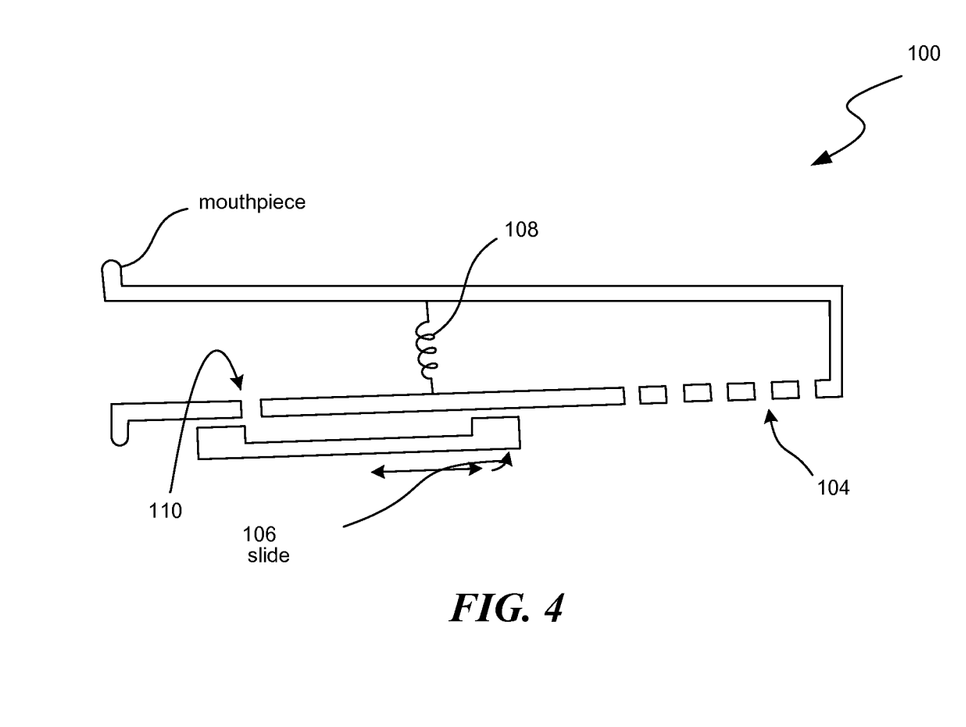
FIG. 4 illustrates a slider used to modulate air flow and vaporization in a device for generating a condensation aerosol.
Figure 5:
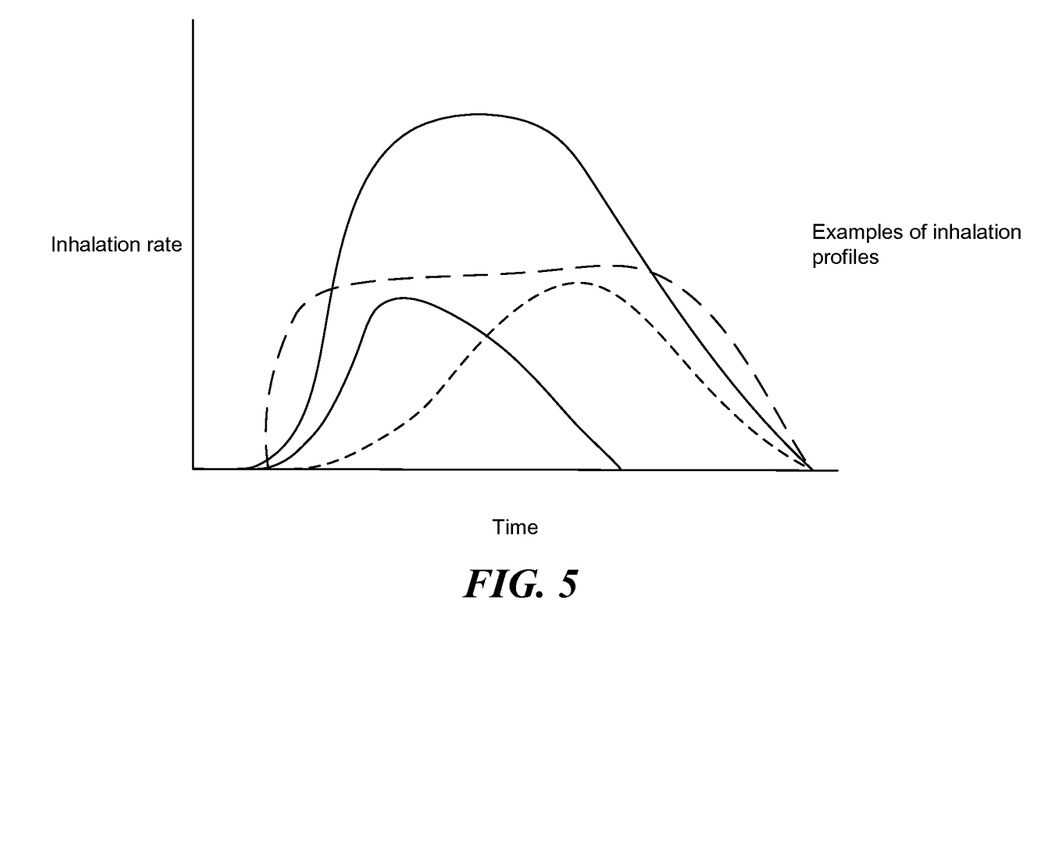
FIG. 5 illustrates a prophetic inhalation profile obtained with a device for generating a condensation aerosol.

A user can switch the inhalation resistance and/or particle size characteristics of the vapor to focus more on the sensory aspects of the vaping experience. It can be advantageous in some settings to use a larger aerosol with little or no exhaled evidence where blowing huge plumes and smoke rings is socially unacceptable. In the device of FIG. 1, the slide 106 can be moved to cover or uncover an air inlet 104 upstream of the heater element 108, or an air inlet 110 downstream of the heater element 108.

The device 100 can have a vaporization chamber 102 and one or more upstream first inlets 104 and a downstream outlet 112. An airflow path 150 is in fluid communication with the vaporization chamber, wherein the airflow path comprises a second inlet 110 configured to permit a substantially laminar flow of air into the airflow path, wherein the second inlet is downstream of the heater element. In some cases, a device of the disclosure comprises a mouthpiece in fluid communication with the vaporization chamber.

The device may include apparatus to modify a size of the outlet 112 and/or the inlet 104 and/or the inlet 110. The apparatus may be positioned upstream of the heater element. In some cases, the apparatus is a baffle, which may be located upstream of the heater element, and optionally configured to slide within the vaporization chamber. A vaporization chamber 102 can be configured to limit a flow of a gas through the airflow path 150 to permit condensation of a vaporized liquid formulation.

A flow meter may be imbedded in a device to measure the inhalation patterns of the user. A flow meter can be a hot wire flow meter, a pressure traducer that measures inhalation vacuum and calculates inhalation rates, or a vane type flow meter that deflects inhalation rates or some other suitable flow meter. The device can have a microprocessor, or a communication device (e.g., Bluetooth) that enables calculation of the optimum parameters of aerosol generation based on the typical inhalation pattern or breathing profile of the user. The device may allow the inhalation profile of the user be customized to the user, such as via the user adjusting parameters of vaporization according to the user's personalized inhalation pattern and breathing profile. Conversely, a device itself can adjust the parameters to more closely match the ideal inhalation characteristics for each individual user/ subject.

Non-limiting examples of parameters that can be adjusted include: (a) an amount of nicotine mixture vaporized; (b) a current applied to the heating element, thereby affecting particle size and the timing of aerosol generation in the inhalation volume; or (c) an inlet opening size, thereby affecting resistance through the device inhalation rates and determining if a mouth or lung breathing maneuver is possible and the inhalation rates. A device can be adjusted for maximum efficiency of delivery of an agent to a user, for "stealthiness" (e.g., a low exhaled fraction), or for visual and sensory effects (e.g., smoke rings, mouth feel, etc.)

Figure 6:
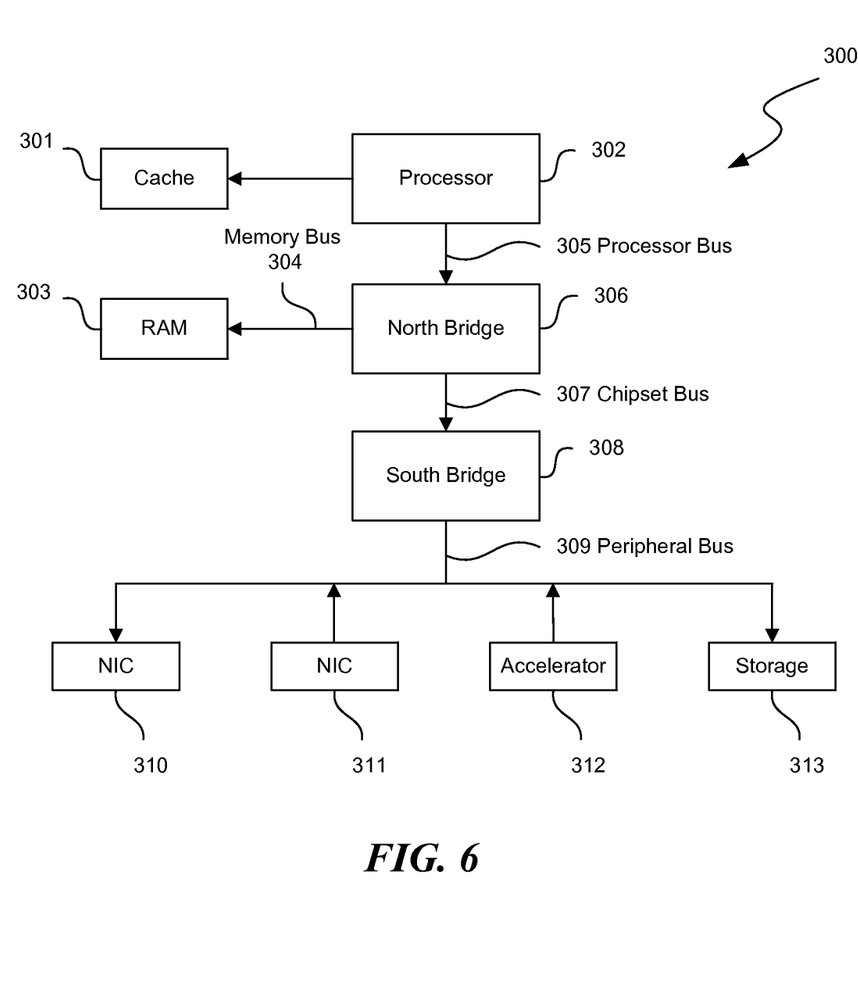
FIG. 6 is a block diagram illustrating a first example architecture of a computer system that can be used with the devices described

Turning to FIG. 6, various computer architectures are suitable for use with an electronically-controlled apparatus and a user interface of the disclosure. FIG. 6 is a block diagram illustrating a first example architecture of a computer system 300 that can be used in connection with example embodiments of the present invention. In FIG. 6, the example computer system can include a processor 302 for processing instructions. Non-limiting examples of processors include: Intel Core i7™ processor, Intel Core i5™ processor, Intel Core i3™ processor, Intel Xeon™ processor, AMD Opteron™ processor, Samsung 32-bit RISC ARM 1176JZ(F)-S v1.0™ processor, ARM Cortex-A8 Samsung S5PC100™ processor, ARM Cortex-A8 Apple A4™ processor, Marvell PXA 930™ processor, or a functionally-equivalent processor. Multiple threads of execution can be used for parallel processing. In some embodiments, multiple processors or processors with multiple cores can be used, whether in a single computer system, in a cluster, or distributed across systems over a network comprising a plurality of computers, cell phones, and/or personal data assistant devices.

As illustrated in FIG. 6, a high speed cache 301 can be connected to, or incorporated in, the processor 302 to provide a high speed memory for instructions or data that have been recently, or are frequently, used by processor 302. The processor 302 is connected to a north bridge 306 by a processor bus 305. The north bridge 306 is connected to random access memory (RAM) 303 by a memory bus 304 and manages access to the RAM 303 by the processor 302. The north bridge 306 is also connected to a south bridge 308 by a chipset bus 307. The south bridge 308 is, in turn, connected to a peripheral bus 309. The peripheral bus can be, for example, PCI, PCI-X, PCI Express, or other peripheral bus. The north bridge and south bridge are often referred to as a processor chipset and manage data transfer between the processor, RAM, and peripheral components on the peripheral bus 309. In some architectures, the functionality of the north bridge can be incorporated into the processor instead of using a separate north bridge chip. The system 300 can include an accelerator card 312 attached to the peripheral bus 309. The accelerator can include field programmable gate arrays (FPGAs) or other hardware for accelerating certain processing.

Software and data are stored in external storage 313 and can be loaded into RAM 303 and/or cache 301 for use by the processor. The system 300 includes an operating system for managing system resources; non-limiting examples of operating systems include: Linux, Windows™, MACOS™, BlackBerry OS™, iOS™, Apple manufactured operating systems and other functionally-equivalent operating systems, as well as application software running on top of the operating system.

In this example, system 300 also includes network interface cards (NICs) 310 and 311 connected to the peripheral bus for providing network interfaces to external storage, such as Network Attached Storage (NAS) and other computer systems that can be used for distributed parallel processing.

Figure 7:
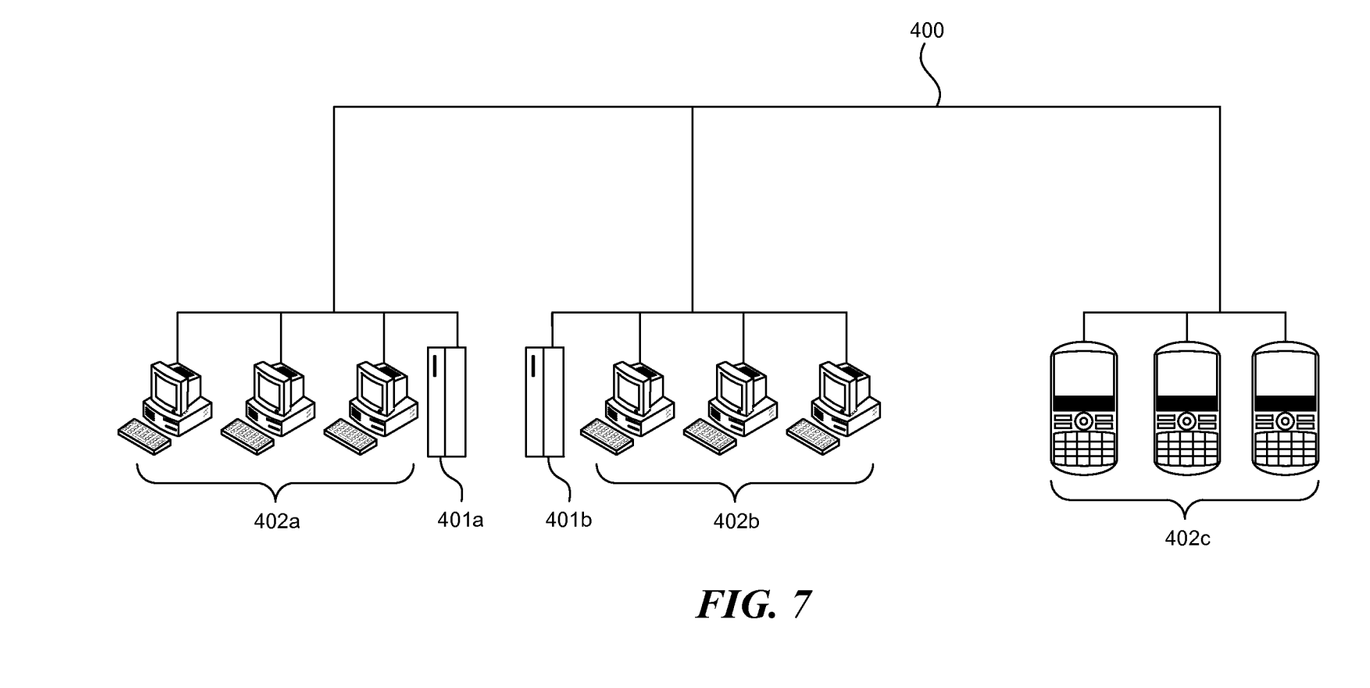
FIG. 7 is a diagram illustrating a computer network.

FIG. 7 is a diagram showing a network 400 with a plurality of computer systems 402a, and 402b, a plurality of cell phones and personal data assistants 402c, and Network Attached Storage (NAS) 401a, and 401b. In some embodiments, systems 402a, 402b, and 402c can manage data storage and optimize data access for data stored in Network Attached Storage (NAS) 401a and 402b. A mathematical model can be used for the data and be evaluated using distributed parallel processing across computer systems 402a, and 402b, and cell phone and personal data assistant systems 402c. Computer systems 402a, and 402b, and cell phone and personal data assistant systems 402c can also provide parallel processing for adaptive data restructuring of the data stored in Network Attached Storage (NAS) 401a and 401b.

Figure 8:
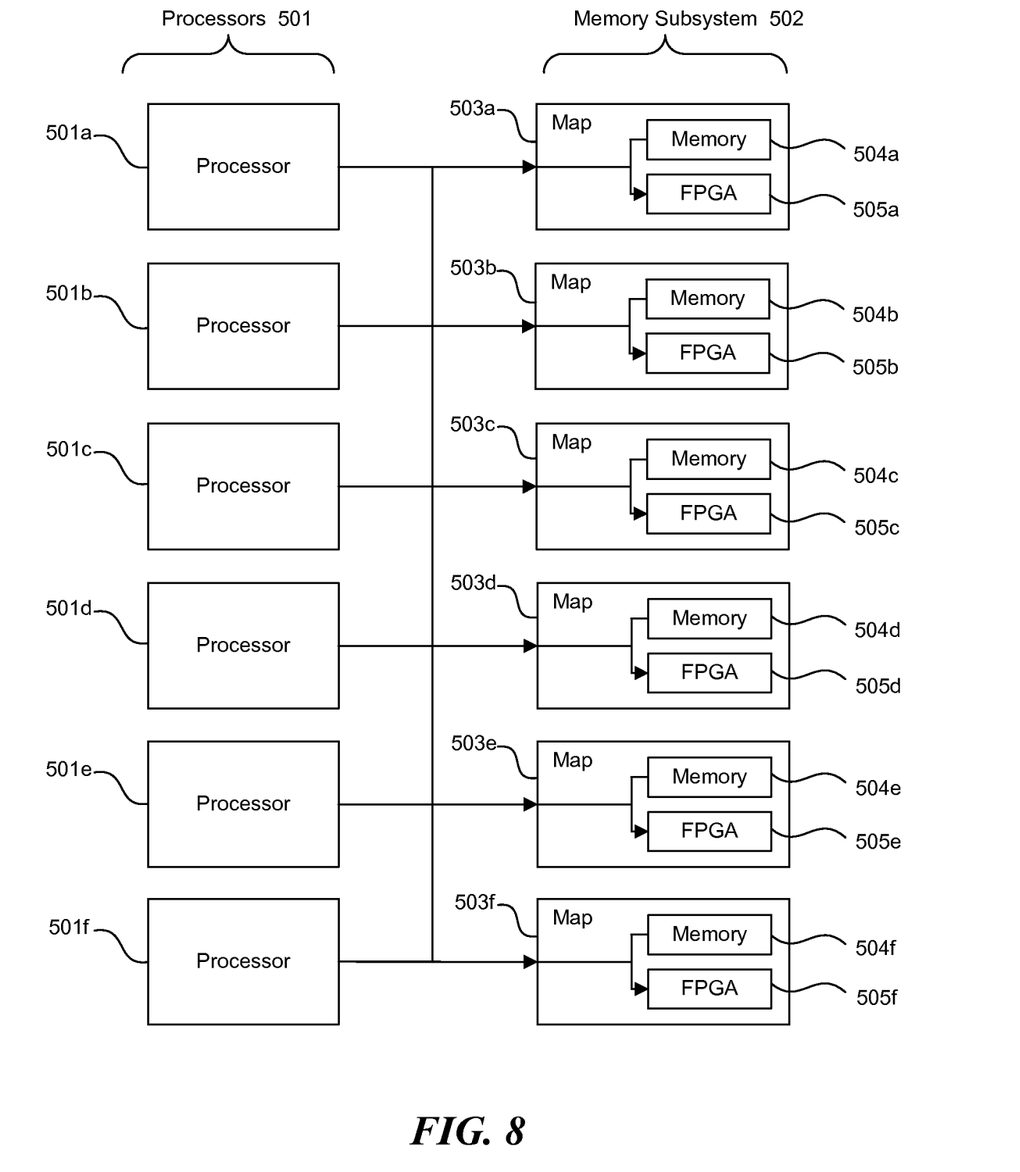
FIG. 8 is a block diagram illustrating a second example architecture of a computer system that can be used in connection with the devices described.

FIG. 8 illustrates an example only, and a wide variety of other computer architectures and systems can be used in conjunction with the various embodiments of the present invention. For example, a blade server can be used to provide parallel processing. Processor blades can be connected through a back plane to provide parallel processing. Storage can also be connected to the back plane or as Network Attached Storage (NAS) through a separate network interface. In some embodiments, processors can maintain separate memory spaces and transmit data through network interfaces, back plane, or other connectors for parallel processing by other processors. In some embodiments, some or all of the processors can use a shared virtual address memory space.

FIG. 8 is a block diagram of a multiprocessor computer system using a shared virtual address memory space. The system includes a plurality of processors 501a-f that can access a shared memory subsystem 502. The system incorporates a plurality of programmable hardware memory algorithm processors (MAPs) 503a-f in the memory subsystem 502. Each MAP 503a-f can comprise a memory 504a-f and one or more field programmable gate arrays (FPGAs) 505a-f. The MAP provides a configurable functional unit and particular algorithms or portions of algorithms can be provided to the FPGAs 505a-f for processing in close coordination with a respective processor. In this example, each MAP is globally accessible by all of the processors for these purposes. In one configuration, each MAP can use Direct Memory Access (DMA) to access an associated memory 504a-f, allowing it to execute tasks independently of, and asynchronously from, the respective microprocessor 501a-f. In this configuration, a MAP can feed results directly to another MAP for pipelining and parallel execution of algorithms.

The above computer architectures and systems are examples only, and a wide variety of other computer, cell phone, and personal data assistant architectures and systems can be used in connection with example embodiments, including systems using any combination of general processors, co-processors, FPGAs and other programmable logic devices, system on chips (SOCs), application specific integrated circuits (ASICs), and other processing and logic elements. Any variety of data storage media can be used in connection with example embodiments, including random access memory, hard drives, flash memory, tape drives, disk arrays, Network Attached Storage (NAS) and other local or distributed data storage devices and systems.

In example embodiments, the computer system can be implemented using software modules executing on any of the above or other computer architectures and systems. In other embodiments, the functions of the system can be implemented partially or completely in firmware, programmable logic devices such as field programmable gate arrays (FPGAs) as referenced in FIG. 8, system on chips (SOCs), application specific integrated circuits (ASICs), or other processing and logic elements. For example, the Set Processor and Optimizer can be implemented with hardware acceleration through the use of a hardware accelerator card, such as accelerator card 312 illustrated in FIG. 6.

Identifying Individualized User Goals

Customized goals can enable the same nicotine delivery platform to be used to achieve multiple beneficial health benefits for different smokers, from full smoking cessation, to partial cessation (e.g., no smoking during the workday), to partial or full nicotine cessation (i.e., stopping nicotine intake entirely), to cognition remediation. In one embodiment, the customized goals enable the same nicotine delivery platform to be used to achieve full smoking cessation. In another embodiment, the customized goals enable the same nicotine delivery platform to be used to achieve full nicotine or smoking cessation without relapse. In another embodiment, the customized goals enable the same nicotine delivery platform to be used to achieve full nicotine withdrawal without nicotine withdrawal symptoms.

eHealth tools can include Web based and mobile tools. For example, for web-based tools, self-report measures can be used to help a smoker or new user of a device provided herein identify a target goal based on their degree of nicotine dependency, health status, health goals, economic goals (i.e., decrease the amount of money spent on cigarettes), target body weight or change in body weight, or other factors. Tests of attentional bias for smoking stimuli, and other cognitive measures of nicotine dependency, can be assessed on the web backend or an electronic nicotine delivery device to assess risk for relapse upon smoking cessation, which can then be used to identify a pattern of use that will minimize the odds of relapse to smoking. In some cases, biomarkers, such as nicotine receptor polymorphisms, information can also be added to a user's profile to help identify the optimal outcome for an individual user.

When a mobile device is used, smoking patterns can be tracked prior to the transition to an electronic nicotine delivery platform, which can enable a real world, ecologically valid assessment of actual behavior to be used as a foundation for a subsequent prescribed pattern of use of an electronic nicotine delivery device.

Customized Feedback

By systematically tracking nicotine administration using an electronic nicotine delivery device described herein, and communicating these results to a web-based backend database, feedback to the user can be customized to help promote the achievement of certain health goals. This customized feedback can be used in multiple ways. For example, achieving certain use patterns (e.g., sufficient nicotine administration to forestall strong cravings after initially transitioning from smoking, or administering a new minimum amount of nicotine in accordance with a planned taper to nicotine cessation) can result in a virtual credit or actual monetary reward that can reinforce the user's pattern of nicotine administration.

Customized feedback can also be used to leverage psychological principles important in smoking cessation. For example, a user could be given feedback that his/her pattern of use is consistent with his/her goals (e.g., quitting smoking) or aim to enhance his/her self-efficacy by demonstrating that the user is becoming less dependent on nicotine based on a real world nicotine challenge presented by an electronic nicotine delivery device described herein (e.g., by administering a test dose containing no nicotine or less nicotine than the user had been administering and demonstrating that their nicotine craving did not increase, or significantly increase, after that challenge dose). Feedback could also engage users using game theory, including the earning of virtual points, which, for example, can be used to enable other actions of the device or to enhance one's standing in a virtual online world, or be redeemed for real-world reinforcements.

In some cases, the electronic nicotine delivery device or web backend system can reinforce a user's self-efficacy by giving him/her feedback that his/her pattern of use is indicative of other users who successfully abstain from smoking. In some cases, an electronic nicotine delivery device or web backend system can give the user feedback that his/her mean nicotine dose is decreasing over time, despite it initially remaining constant or nearly constant, so as to enhance self-efficacy and increase his/her resilience in the face of environmental smoking cues that could otherwise trigger a smoking lapse or relapse "About" can mean a referenced numeric indication plus or minus 10% of that referenced numeric indication. For example, the term about 4 can include a range of 3.6 to 4.4.

The invention claimed is:

1. A device for generating an aerosol, comprising:
a vaporization chamber having at least one upstream inlet and a downstream outlet;
a heater in the vaporization chamber between the upstream inlet and the downstream outlet;
a downstream inlet in the vaporization chamber downstream of the heater; and
a baffle slide slidable within the vaporization chamber, the baffle slide upstream of the heater to divert air around the heater.

2. A device for generating an aerosol, comprising:
a mouthpiece on a housing;
a vaporization chamber in the housing, the vaporization chamber having at least one upstream inlet and a downstream outlet;
a heater in the vaporization chamber between the upstream inlet and the downstream outlet;
a downstream inlet in the vaporization chamber downstream of the heater;
a baffle slide slidable within the vaporization chamber in a direction parallel to a longitudinal axis of the device;
the baffle slide upstream of the heater to divert air around the heater.

* * * * *